(12) United States Patent
Schmidt et al.

(10) Patent No.: US 8,883,084 B2
(45) Date of Patent: Nov. 11, 2014

(54) SILOXANE REMOVAL VIA SILICATE FORMATION FOR LIFETIME EXTENSION OF PHOTOCATALYTIC DEVICES

(75) Inventors: Wayde R. Schmidt, Pomfret Center, CT (US); Treese Campbell-Hugener, Coventry, CT (US); Tania Bhatia, Middletown, CT (US)

(73) Assignee: Carrier Corporation, Farmington, CT (US)

( * ) Notice: Subject to any disclaimer, the term of this patent is extended or adjusted under 35 U.S.C. 154(b) by 134 days.

(21) Appl. No.: 12/669,311

(22) PCT Filed: Jul. 31, 2007

(86) PCT No.: PCT/US2007/017113
§ 371 (c)(1),
(2), (4) Date: Jan. 15, 2010

(87) PCT Pub. No.: WO2009/017480
PCT Pub. Date: Feb. 5, 2009

(65) Prior Publication Data
US 2010/0183484 A1 Jul. 22, 2010

(51) Int. Cl.
*B01J 19/08* (2006.01)
*B01J 35/00* (2006.01)
*A61L 9/20* (2006.01)
*B01D 53/86* (2006.01)

(52) U.S. Cl.
CPC .............. *A61L 9/205* (2013.01); *B01J 35/004* (2013.01); *B01D 2257/708* (2013.01); *B01D 2255/206* (2013.01); *B01D 2255/802* (2013.01); *A61L 2209/14* (2013.01); *B01D 53/8687* (2013.01)
USPC ........ 422/186.3; 423/610; 502/300; 502/350; 201/748.01; 201/748.1; 201/748.14; 252/186.1; 510/348

(58) Field of Classification Search
CPC ..... A61L 9/015; A61L 9/205; A61L 2209/14; A61L 9/22; B01D 53/8687
USPC ................ 422/186.3; 502/300, 350; 423/610; 210/748.01, 748.1, 748.14; 252/186.1; 510/348
See application file for complete search history.

(56) References Cited

U.S. PATENT DOCUMENTS 5,919,726 A 7/1999 Hatano et al.
6,037,289 A 3/2000 Chopin et al.
(Continued)

FOREIGN PATENT DOCUMENTS

CA 2141921 * 8/1995
CA 2314381 * 2/2001
(Continued)

OTHER PUBLICATIONS

Pal et al "Preparation and charactrization of TiO2/Fe2O3 binary mixed oxides and its photo-catalytic properties", Material Chemistry and Physics 59 (1999) p. 254-261.*

(Continued)

*Primary Examiner* — Xiuyu Tai
(74) *Attorney, Agent, or Firm* — Cantor Colburn LLP

(57) ABSTRACT

A photocatalytic device for reacting with volatile organic compounds includes a photocatalyst and at least one additive, such as hafnium oxide and zirconium oxide, that is capable of forming a stable silicate with silicon dioxide. The additive reacts with volatile silicon-containing compounds to form stable silicate compounds. As a result, the silicon-containing compounds are unavailable for deactivation of the photocatalyst.

14 Claims, 3 Drawing Sheets

(56) References Cited

U.S. PATENT DOCUMENTS

| | | | |
|---|---|---|---|
| 6,221,259 B1 | 4/2001 | Kittrell | |
| 6,414,213 B2 | 7/2002 | Ohmori et al. | |
| 6,436,542 B1* | 8/2002 | Ogino et al. | 428/432 |
| 6,908,881 B1* | 6/2005 | Sugihara | 502/350 |
| 2001/0046937 A1* | 11/2001 | Murasawa et al. | 502/150 |
| 2002/0169076 A1* | 11/2002 | Takeshi et al. | 502/350 |
| 2003/0232186 A1* | 12/2003 | Matsuda et al. | 428/325 |
| 2004/0241040 A1 | 12/2004 | Wei et al. | |
| 2004/0245496 A1* | 12/2004 | Taoda | 252/186.1 |
| 2004/0258581 A1 | 12/2004 | Wei et al. | |
| 2004/0265587 A1 | 12/2004 | Koyanagi et al. | |
| 2006/0188432 A1* | 8/2006 | Shio | 423/610 |
| 2006/0280660 A1* | 12/2006 | Weiss | 422/186.3 |

FOREIGN PATENT DOCUMENTS

| | | |
|---|---|---|
| CN | 1805780 A | 7/2006 |
| EP | 1066878 A1 | 1/2001 |
| EP | 1118385 A1 | 7/2001 |
| EP | 1153999 A1 | 11/2001 |
| WO | WO2007136363 A2 | 11/2007 |

OTHER PUBLICATIONS

International Search Report and Written Opinion of the Patent Cooperation Treaty in counterpart foreign Application No. PCT/US2007/017113, filed Jul. 31, 2007.

Extended European Search Report for European Application No. 078363671.0 dated Jun. 4, 2013, 10 pages.

* cited by examiner

SILOXANE REMOVAL VIA SILICATE FORMATION FOR LIFETIME EXTENSION OF PHOTOCATALYTIC DEVICES

CROSS-REFERENCE TO RELATED APPLICATION(S)

This application claims the benefit of PCT Application No. PCT/US2007/017113 filed Jul. 31, 2007, entitled "SILOXANE REMOVAL VIA SILICATE FORMATION FOR LIFETIME EXTENSION OF PHOTOCATALYTIC DEVICES".

BACKGROUND

This invention relates generally to use of ultraviolet photocatalytic oxidation (UV-PCO) technology for improved decontamination of fluid in fluid purifier systems, especially in air purifier systems. More specifically, the present invention relates to a device for reducing the deactivation of photocatalytically active oxides used in UV-PCO technology by volatile silicon-containing compounds.

Some buildings utilize air purification systems to remove airborne substances such as benzene, formaldehyde, and other contaminants from the air supply. Some of these purification systems include photocatalytic reactors that utilize a substrate or cartridge containing a photocatalyst oxide. When placed under an appropriate light source; typically a UV light source, the photocatalyst oxide interacts with airborne water molecules to form hydroxyl radicals. The hydroxyl radicals then attack the contaminants and initiate an oxidation reaction that converts the contaminants into less harmful compounds, such as water and carbon dioxide. It is further believed that the combination of water vapor, suitably energetic photons and a photocatalyst also generates an active oxygen agent like hydrogen peroxide (W. Kubo and T. Tatsuma, Analytical Sciences 20 2004 591-593).

A commonly used UV photocatalyst is titanium dioxide ($TiO_2$), otherwise referred to as titania. Degussa P25 titania and tungsten oxide grafted titania catalysts (such as tungsten oxide on P25) have been found to be especially effective at removing organic contaminants under UV light sources.

A problem with air purification systems using UV-PCO technology has arisen. Currently available systems exhibit a significant loss in catalytic ability over time. This loss of catalytic ability has been attributed to volatile silicon-containing compounds (VSCCs), such as certain siloxanes, in the air.

The aggregate amount of volatile organic compounds (VOCs) in air is typically on the order of 1 part per million by volume. In contrast, VSCC concentrations are two or more orders of magnitude lower. These VSCCs arise primarily from the use of certain personal care products, such as deodorants, shampoos, and the like, or dry cleaning fluids. They can also arise from the use of RTV silicone caulks, adhesives and the like. When these VSCCs are oxidized on the photocatalyst of a UV-PCO system, they form relatively non-volatile compounds containing silicon and oxygen that may deactivate the photocatalyst. Examples of non-volatile compounds of silicon and oxygen include silicon dioxide, silicon oxide hydride, silicon hydroxide, high order polysiloxanes and the like. These compounds may be at least partially hydrated when water vapor is present. Increasing the catalyst surface area does not necessarily slow the rate of deactivation as might be expected if the deactivation occurred by direct physical blockage of the active sites by the resultant non-volatile compound containing silicon and oxygen.

There is a need for improved UV-PCO systems that can aid in the elimination of fluid borne contaminants in a fluid purifier and can operate effectively in the presence of typically encountered levels of volatile silicon-containing compounds such as siloxanes.

SUMMARY

A photocatalytic device includes photocatalyst in conjunction with an additive that protects the photocatalyst from deactivation caused by volatile silicon-containing compounds. The additive includes particles or crystals of one or more compounds capable of forming a stable silicate or solid solution with inorganic compounds containing silicon and oxygen, such as silicon dioxide. The additive, which may be interspersed with the photocatalyst or may be in the form of islands or an incomplete overlayer on a photocatalyst layer or a photocatalyst particle, reacts with volatile or semivolatile silicon-containing compounds or their oxidation product(s) to form a stable silicate or solid solution. The additive sequesters the silicon-containing contaminants from the photocatalyst, so that they are not available to react with and deactivate the photocatalyst. Examples of additives include hafnia ($HfO_2$), zirconia ($ZrO_2$), niobia ($Nb_2O_5$), alumina ($Al_2O_3$), magnesia (MgO), yttria ($Y_2O_3$), tantala ($Ta_2O_5$), ytterbia ($Yb_2O_3$), chromia ($Cr_2O_3$), scandia ($Sc_2O_3$), other rare earth oxides and mixtures and combinations of these compounds, for example yttrium stabilized zirconia and hafnia.

DETAILED DESCRIPTION

Figure 1:
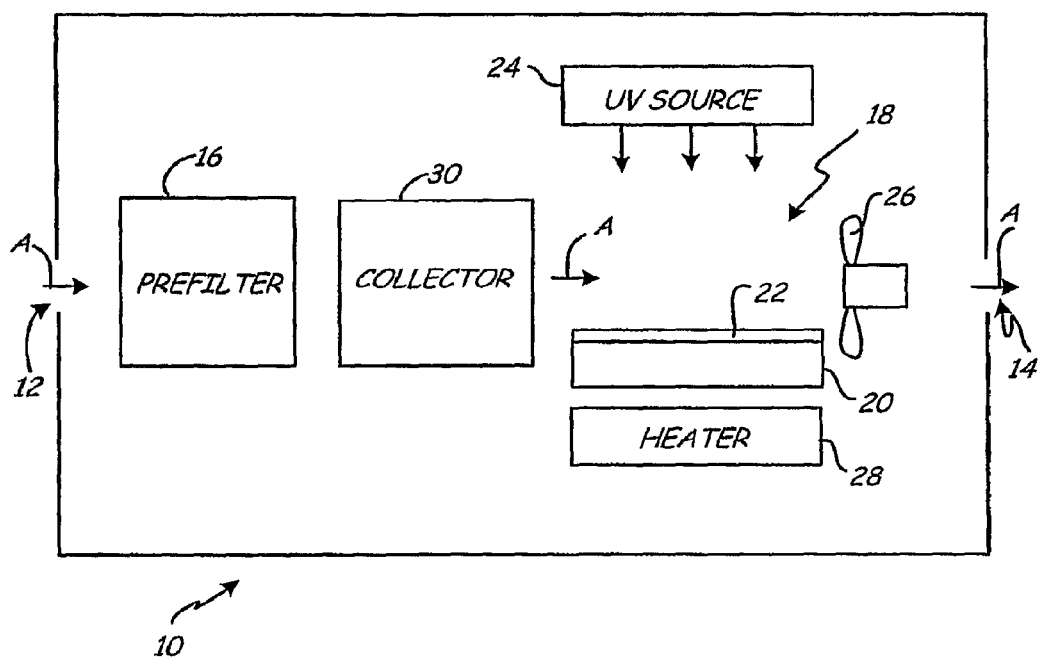
FIG. 1 schematically illustrates a photocatalytic air purification device.

FIG. 1 is a schematic diagram of air purifier system 10, which uses ultraviolet photocatalytic oxidation (UV-PCO) to remove contaminants from air. Air purifier system 10 includes inlet 12, outlet 14, photocatalytic reactor 18 (which includes substrate 20, photocatalytic coating 22, UV source 24), fan 26 and heater 28. An optional collector 30 may be used to temporarily collect certain volatile compounds such as VOCs prior to transfer through the photocatalytic reactor 18. For example, an adsorbent bed (e.g. activated carbon, zeolites, etc.) may be used to collect VOCs for subsequent release (e.g. through heating and subsequent volatilization of the collected VOCs) into the photocatalytic reactor 18. Collector 30 may be integrated or incorporated into prefilter 16.

Ambient air is drawn into the system 10 through inlet 12 by fan 26. Airstream A passes through prefilter 16, and then through photocatalyst reactor 18 and fan 26 to outlet 14. Prefilter 16 removes dust and particles by trapping the dust and particles. Within photocatalyst reactor 18, ultraviolet radiation from UV source 24 is absorbed by photocatalyst coating 22, which causes photocatalyst coating 22 to interact with airborne water molecules to produce reactive species such as hydroxyl radicals, hydrogen peroxide, hydrogen peroxide radicals, and superoxide ions. These reactive species interact with VOCs in the air to transform the VOCs into byproducts such as carbon dioxide and water. Therefore, airstream A contains less contaminants as it exits system 10 through outlet 14 than it contained when it entered system 10 through inlet 12.

In FIG. 1 substrate 20 is illustrated schematically as a flat plate. In practice, substrate 20 can take a number of different forms, which may be configured to maximize the surface area on which photocatalytic coating 22 is located or to maximize the extent of nonlaminar flow through the substrate. One example is a honeycomb structure on which photocatalytic coating 22 is deposited and through which airstream A passes. Another example is a segmented and radially offset array of discrete honeycomb structures on which photocatalytic coating 22 is deposited and through which airstream A passes.

Experimental evidence has highlighted the need to protect the photocatalyst coating 12 from contamination and deactivation by volatile silicon-containing compounds. The major source of these VSCCs is believed to be the family of compounds containing volatile methyl siloxanes (VMS) commonly found in cleaners, personal deodorants, shampoos, and a variety of other personal and commercial products. Common members of the VMS family include hexamethyl cyclotrisiloxane and octamethyl cyclotetrasiloxane, often referred to $D_3$ and $D_4$, respectively. Larger molecules $D_5$, $D_6$, $D_7$ and so on are also known. Related volatile silicon-containing compounds, including linear siloxanes, are also of concern.

It is most desirable to remove VSCCs from the incoming air stream upstream of photocatalytic reactor 18, but it is also important to protect photocatalytic reactor 18 from any VSCCs in the air stream that reach photocatalytic reactor 18 and come in contact with photocatalyst coating 22.

In the present invention, additives intermixed with the photocatalyst within photocatalyst coating 22, or deposited on the surface of photocatalyst coating 22 in the form of islands or an incomplete layer act as sequestering agents to prevent VSCCs from reaching the photocatalyst and contaminating or deactivating it. The additives include one or more compounds that are capable of reacting with VSCCs to form a stable silicate(s) or solid solution(s) with inorganic compounds containing silicon and oxygen, such as silicon dioxide. As a result, the additives permanently remove the VSCCs from the air stream and prevent them from contacting and deactivating the photocatalyst.

Examples of additives capable of forming a stable silicate with silicon dioxide include hafnia ($HfO_2$), zirconia ($ZrO_2$), alumina ($Al_2O_3$), magnesia (MgO), yttria ($Y_2O_3$), tantala ($Ta_2O_5$), ytterbia ($Yb_2O_3$), chromia ($Cr_2O_3$), scandia ($Sc_2O_3$), other rare earth oxides and mixtures of these compounds. Specific oxide systems containing $HfO_2$ and $ZrO_2$ will form stable silicates with $SiO_2$, for example $HfSiO_4$ and $ZrSiO_4$, respectively. These silicate compounds are stable line compounds in the phase diagrams of these binary systems, and therefore will lock up the silicon-containing species and render them unavailable for deactivation of the nearby $TiO_2$ based photocatalyst. MgO forms a stable line compound $MgSiO_3$ with $SiO_2$. Other oxides form stable silicates with $SiO_2$ without forming line compounds (e.g. solid solutions, $Nb_2O_5$, $Ta_2O_5$ and $Cr_2O_3$). Other oxides form stable silicates with $SiO_2$ yet form more than one line compound with $SiO_2$ (e.g. $Y_2O_3$, $Yb_2O_3$, and $Sc_2O_3$). Titanium dioxide ($TiO_2$) does not form a similarly stable line compound with $SiO_2$.

Figure 2:
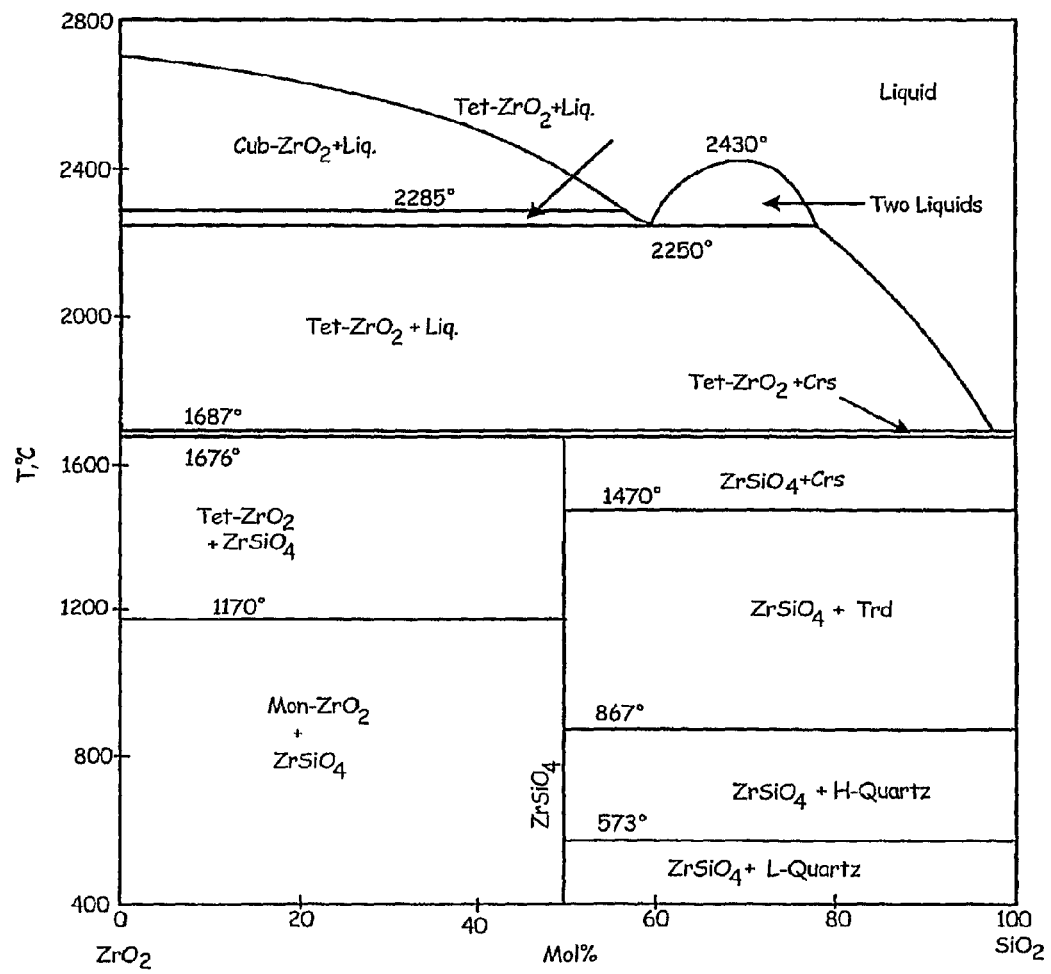
FIG. 2 is a phase diagram of the $ZrO_2/SiO_2$ system.
Figure 3:
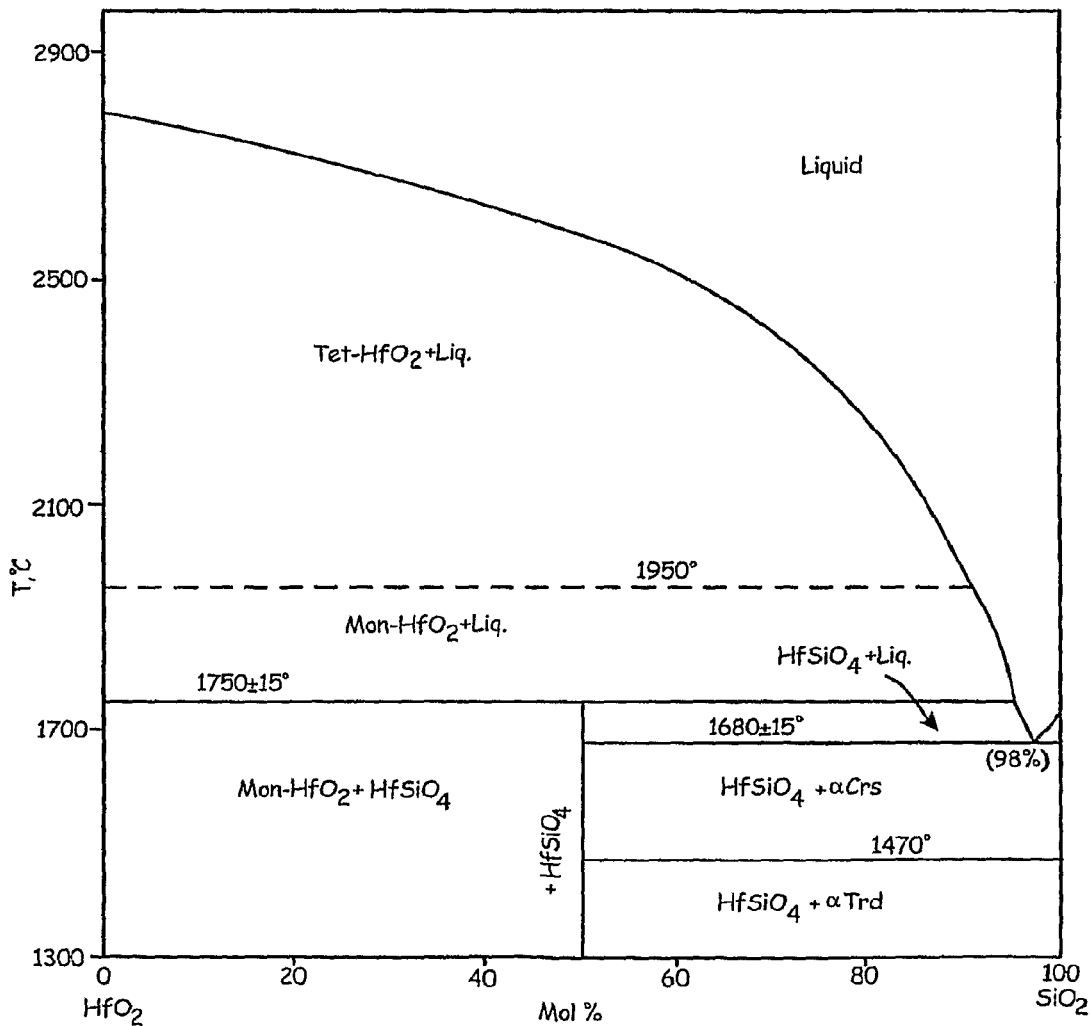
FIG. 3 is a phase diagram of the $HfO_2/SiO_2$ system.

Phase diagrams for the zirconia and hafnia systems are shown in FIGS. 2 and 3, respectively. In both cases, the stable line silicate forms at an equal molar ratio (1:1) of the end member oxides (for example $ZrO_2/SiO_2$ and $HfO_2/SiO_2$). The phase diagrams show that a stable silicate will be present in all compositions containing $SiO_2$. Free silica (as quartz) will only be present above a 50 mol percent level of silica. Thermodynamic data for the reaction of $ZrO_2+SiO_2=ZrSiO_4$ indicates the reaction is favorable ($\Delta G<0$) for the temperature range of 0° C. to about 1700° C. An analogous reaction based on $HfO_2$ can be expected to behave similarly.

A photocatalyst coating with an additive capable of forming a stable silicate can be produced in a variety of different ways. Some examples are as follows:

First, a photocatalyst layer having interspersed additive particles can be formed by separately producing photocatalyst particles and additive particles. The additive, such as $ZrO_2$, $HfO_2$, mixed $ZrO_2/HfO_2$, yttria or magnesia stabilized zirconia, rare earth modified $ZrO_2$ or $HfO_2$ or other suitable oxides or mixture of oxides can be added as a particulate filler in a slurry containing the photocatalyst prior to coating deposition. The slurry is typically an aqueous slurry that is coated onto the substrate and then dried to produce the photocatalyst coating. The additive particles are dispersed within the coating, and provide sites at which volatile silicon-containing compounds can react to form a stable silicate. Additive particles can be uniformly sized or bi- or multimodally distributed and may be sized similarly to or different than the photocatalytic particles. Dispersants, pH modifiers, surfactants and the like may be used to adjust the properties of the slurry to render it suitable for processing.

Second, a mixture of the photocatalyst and the additives can be created with a sol-gel or co-precipitation method by the use of appropriate precursors. An example of a process for forming a photocatalyst using a sol-gel process is described in PCT application PCT/US07/12882 entitled "Deactivation Resistant Photocatalyst and Method of Preparation" filed May 31, 2007, which is incorporated by reference.

A sol-gel process for forming photocatalyst coatings with intermixed additives can follow the same general steps described in the above-mentioned PCT application. Template creation begins with the addition of a first precursor to a solution to produce a first controlled hydrolysis reaction. The first precursor includes, for example, a zirconium-containing precursor or hafnium-containing precursor, or both, or another oxide precursor or mixture of precursors selected to provide the appropriate metal species. The solution may include one or more low molecular weight polymer components, and one or more salts.

After the first hydrolysis reaction is complete, a second precursor is added to the solution in order to form the photocatalyst. The second precursor, may be, for example, a titanium-containing precursor. One or more metal salts may also be added to the solution to ultimately form a wide band gap metal oxide semiconductor in addition to titanium dioxide. Examples of metal salts include salts of tin, iron, neodymium, zinc and cerium.

After the second hydrolysis reaction is complete, the sol is aged, and then template conditioning occurs. The template conditioning can include filtration, reflux, and rotoevaporation.

Next, template refinement occurs. This includes an optional drying step and calcination of the photocatalyst and additive particles. The result of the calcination step is a powder containing particles of the photocatalyst and particles of the additive. An aqueous slurry is then formed from the powder and is applied to the substrate by spraying, dip coating, or other application technique. Dispersants, pH modifiers, surfactants and the like may be used as mentioned previously to adjust the properties of the slurry to render it suitable for processing. After the solvent evaporates, the resulting coating includes the photocatalyst with intermixed particles of the additive.

Third, the photocatalyst coating, with the additives, can be in the form of multiple layers. For example, the photocatalyst layer can be deposited first, followed by a coating of the additive. The additive layer is an incomplete layer that does not cover the entire surface of photocatalyst. Instead, the resulting additive layer is in the form of islands of additive material on the surface of the photocatalyst. Formation of the islands or incomplete layer can be produced, for example, by vapor deposition, aerosol spray or solution precipitation techniques.

In some embodiments, the photocatalyst is titanium dioxide (titania) together with at least one other wide band gap semiconductor such as tin oxide, indium oxide, zinc oxide, iron oxide, neodymium oxide and cerium oxide. The photocatalyst may have enhanced resistance to deactivation by VSCCs by being formed of porous particles having a porous structure with pores of a diameter greater than about 6 nm and less than five populations of discrete pore size distributions. The porous particles are formed by crystallites that preferably are anatase titania, and have diameters of about 0.1 micron. The crystallites have diameters greater than about 2 nm.

In some embodiments, the additive particles can be in the form of dispersed, fine metal particles (e.g. Zr, Hf, Y, Al, etc.) that are selected for their potential to form oxides with relatively high reactivity towards, and therefore better scavenging ability of, the silicon-containing species.

In order to facilitate a reaction of the additive with volatile silicon-containing compounds to form a stable silicate, photocatalyst coating 22 may be temporarily or continually operated at an elevated temperature. The heating of photocatalyst coating 22 can be achieved by heater 28, for example, using resistive heating, microwave heating, infrared heating or a combination of these or similar heating methods.

Although the present invention has been described with reference to preferred embodiments, workers skilled in the art will recognize that changes may be made in form and detail without departing from the spirit and scope of the invention.

The invention claimed is:

1. An air purification system comprising:
   a substrate;
   a photocatalyst layer on the substrate, comprising photocatalytically active titanium dioxide particles;
   metal oxide additive particles capable of forming a stable silicate or solid solution with volatile silicon-containing compounds, said metal oxide additive particles including at least one of a hafnium oxide, a yttrium oxide, a tantalum oxide, a ytterbium oxide, and a scandium oxide, and disposed as islands on top of the photocatalyst layer or as an incomplete overlayer on the photocatalyst layer; and
   a UV source for illuminating the photocatalyst layer.

2. The system of claim 1, wherein the photocatalytically active titanium dioxide particles consist essentially of titanium dioxide.

3. The system of claim 1, wherein the photocatalytically active titanium dioxide particles further comprise a wide band gap oxide semiconductor other than titanium dioxide.

4. The system of claim 1, wherein the additive particles are disposed as the incomplete overlayer on the photocatalyst layer.

5. The system of claim 1, wherein the additive particles are disposed as the islands on top of the photocatalyst layer.

6. An ultraviolet photocatalyst comprising:
   a photocatalyst layer of porous particles comprising titanium dioxide crystallites;
   particles comprising a sequestering agent positioned adjacent the porous particles of the photocatalyst layer, the sequestering agent capable of reacting with volatile silicon-containing compounds to form a stable silicate or solid solution and including at least one of a hafnium oxide, a yttrium oxide, a tantalum oxide, a ytterbium oxide, and a scandium oxide
   wherein the particles of the sequestering agent form an incomplete overlayer on a surface of the photocatalyst layer, or the particles of the sequestering agent form islands on top of at least a portion of the photocatalyst layer.

7. The photocatalyst of claim 6, wherein the crystallites have a diameter greater than about 2 nm.

8. The photocatalyst of claim 6, wherein the porous structure has pores of a diameter equal to or greater than about 6 nm.

9. The photocatalyst of claim 6, wherein the crystallites form porous particles of about 0.1 micron diameter.

10. The photocatalyst of claim 6 wherein the particles of the sequestering agent form the incomplete overlayer on the surface of the photocatalyst layer.

11. The photocatalyst of claim 6 wherein the particles of the sequestering agent form the islands on top of at least the portion of the photocatalyst layer.

12. A photocatalytic device comprising:
   a substrate;
   a photocatalyst layer on the substrate, the photocatalyst layer including photocatalytically active particles comprising photocatalytically active titanium dioxide capable of reacting with volatile organic compounds; and
   sequestering particles capable of reacting with volatile silicon-containing compounds to form a stable silicate or solid solution, the sequestering particles including at least one of a hafnium oxide, a yttrium oxide, a tantalum oxide, a ytterbium oxide, and a scandium oxide, and being disposed as islands on top of the photocatalyst layer or as an incomplete overlayer on the photocatalyst layer.

13. The photocatalytic device of claim 12, wherein the sequestering particles are disposed as the islands on top of the photocatalyst layer.

14. The photocatalytic device of claim 12, wherein the sequestering particles are disposed as the incomplete overlayer on the photocatalyst layer.

* * * * *